United States Patent
Desarnaud

(10) Patent No.: US 6,450,026 B1
(45) Date of Patent: Sep. 17, 2002

(54) CAPACITIVE SENSORS FOR MEASURING HUMIDITY AND METHOD OF MAKING SAME

(76) Inventor: Jean Desarnaud, 4 Rue Hoche, 92170 Vanves (FR)

( * ) Notice: Subject to any disclaimer, the term of this patent is extended or adjusted under 35 U.S.C. 154(b) by 0 days.

(21) Appl. No.: 09/582,768
(22) PCT Filed: Jun. 30, 2000
(86) PCT No.: PCT/FR97/02467
§ 371 (c)(1), (2), (4) Date: Dec. 18, 2000
(87) PCT Pub. No.: WO99/35488
PCT Pub. Date: Jul. 15, 1999

(51) Int. Cl.[7] .......................... G01N 27/22; G01D 5/24; H01G 4/00; H01G 4/256
(52) U.S. Cl. .................... 73/335.04; 324/663; 324/664; 324/689; 324/361; 324/271; 324/286; 324/427; 324/79
(58) Field of Search ..................... 73/335.04; 29/25.03; 324/663, 664, 689, 694; 338/35; 361/271, 286; 427/79

(56) References Cited

U.S. PATENT DOCUMENTS

| | | | |
|---|---|---|---|
| 4,276,128 A | * | 6/1981 | Nishino et al. .......... 73/335.04 |
| 4,305,112 A | * | 12/1981 | Heywang et al. ........ 73/335.04 |
| 4,482,581 A | * | 11/1984 | Lorin et al. .................... 427/79 |
| 5,177,662 A | * | 1/1993 | Thoma ..................... 73/335.04 |
| 5,812,367 A | * | 9/1998 | Kudoh et al. .............. 29/25.03 |

FOREIGN PATENT DOCUMENTS

| | | | | |
|---|---|---|---|---|
| DE | 3209990 | * | 8/1983 | |
| EP | 10771 | * | 5/1980 | .............. 73/335.04 |
| EP | 58102 | * | 8/1982 | .................. 427/79 |
| FR | 2750494 | * | 1/1998 | .............. 73/335.04 |
| GB | 2017924 | * | 10/1979 | .............. 73/335.04 |

* cited by examiner

*Primary Examiner*—Daniel S. Larkin
(74) *Attorney, Agent, or Firm*—Sughrue Mion, PLLC

(57) ABSTRACT

The invention concerns a sensor comprising two electrodes (1, 3a) separated by a dielectric material (2). One electrode (3a) being produced by using a non-porous metal sheet, the other electrode (1) being advantageously made of a non-metallic porous material made conductive and the dielectric material being advantageously in the form of a multilayer polymer film (2). The resulting sensor can be adjusted to the desired value by a particular capacitor by reducing the useful surface of the porous electrode (1). The reduction step carried out by simply scraping or eroding the material constituting the porous electrode (1).

23 Claims, 1 Drawing Sheet

CAPACITIVE SENSORS FOR MEASURING HUMIDITY AND METHOD OF MAKING SAME

BACKGROUND OF THE INVENTION

The invention relates to a new technology for producing capacitive sensors, more particularly for carrying out relative humidity measurements. It will be seen that the technology and embodiments described within the scope of the present invention may be applied to the production of sensors which may be used for carrying out other measurements.

Several methods for producing capacitive sensors are known as well as the use of such sensors for carrying out humidity measurements.

The technology used here consists in producing two plane electrodes, electrodes between which a material is placed, the dielectric characteristics of which are changed by the presence (or absence) of humidity in the ambient air. The change in characteristics of the dielectric causes a variation of the capacity of the thereby produced condenser, so that the output signal gives information on the air's humidity content. Processing this output signal does not pose any particular problem, for example this is achieved with a R-C or R-L-C circuit.

According to a prior art technique, one of the electrodes is produced by depositing a metal layer on an insulating substrate and the other one by depositing a thin metal layer on the dielectric. In a commonly used embodiment, vacuum metallizing is performed which gives a very low metal thickness. Indeed, to have a capacitive. sensor function as a humidity sensor, the humid air which is to be characterized must absolutely be able to penetrate into the inside of the condenser in order to influence the dielectric. Consequently, it is realized that a particularly thin porous electrode should be produced. If this electrode is made of metal, and taking into account the atomic structure of metals, the limit between electrical continuity and imperviousness is reached for thicknesses of the order of $1/100$ micron, and this, whichever metal is used (generally, chromium, nickel, or gold). In addition to a relative brittleness of the sensor, this embodiment involves many disadvantages; in particular, making a reliable connection between this particularly thin electrode and the measurement circuit is extremely delicate. Besides, it is seen that presently produced capacitive sensors require a succession of careful and delicate operations; first, metal is coated on a substrate and this on two distinct areas, one area serves as a first electrode and the other one is used as a contact for the second electrode. The whole is then covered by a dielectric film which is interrupted at the contact area provided, for the second electrode. Finally, the second electrode is put into place, i.e. by depositing a metal film on a thickness of the order of one hundredth of a micron. Of course, an adjustment of the useful surface of at least one electrode is required in order to obtain the desired capacity for a given moisture content. Different methods have been suggested for achieving this post-calibration; particularly, French patent FR-2 687 834 (CORECI) is to be mentioned which provides a plurality of bridges capable of being disconnected as well as British patent GB-2 213 323 (VAISALA) which recommends adjusting the useful surface of an electrode by insulating it through the substrate by a laser process without altering the dielectric. In every case, the method is the same; a capacitive sensor is produced according to the above described method, taking a maximum of precautions, then its performances are measured and absolutely necessary adjustments are made in order to obtain a usable response.

In any case, capacitive sensors produced according to the above described methods, tend to behave like "sponges", i.e. their constituent materials are impregnated with moist air (notably at the substrate/metal interface of the first electrode) so that they exhibit a certain hysteresis and their response may be erroneous in minutes or hours following their exposure to an atmosphere saturated with humidity, or even their immersion in a liquid.

The imperfect and unsatisfactory character of the capacitive sensor for measurement of humidity is now particularly convincing: the sensors are particularly brittle, their accuracy is of the order of 10% on the measured value, they are not interchangeable, they are subject to saturation and their manufacturing process is both long, delicate,and expensive.

Another type of capacitive sensor for measuring humidity is described in document US-5177 662. This sensor comprises two porous electrodes produced as a porous polymer layer which has been made conductive by inclusion of conductive particles, such as carbon particles. However, the effective resistance of these electrodes is of the order of 15,000 $\Omega$.

The used dielectric is an absorbing polymer film with a thickness of about 10 $\mu$m, such as polyimide or polyparabanic acid.

This sensor, therefore, has an entirely porous structure.

SUMMARY OF THE INVENTION

The invention is directed to producing sensors which overcome the aforementioned drawbacks.

An object of the present invention is to produce a capacitive sensor for measuring humidity whereby manufacture thereof is simplified, especially at the level of assembling the electrodes and the dielectric and fixing the contacts for tapping information.

Another object of the invention is to allow for provision of particularly robust and reliable capacitive sensors which notably are not subject to deterioration or alteration of their characteristics as a result of freezing-thawing cycles or after immersion.

Another object of the invention is to allow for production of flexible sensitive elements, adaptable to supports of skewed or curved shape.

An additional object of the invention is to allow for production of independent sensitive elements directly connectible to passive or active measurement circuits.

Another object of the invention is to provide sensors exhibiting manufacturing tolerances for the basic values of the order of 0.25%, allowing for interchangeability without recalibration with a metrological tolerance of the order of 1%.

An additional object of the invention is to provide capacitive sensors which exhibit retention of their performances and instantaneous desaturation after a saturation phase (100% R.H.) maintained for a long period.

The final object of the invention is to provide humidity sensors for which the performances(accuracy, robustness, reproducibility, reliability)/price ratio is enhanced very substantially as compared to existing technologies. This should allow access to mass production applications such as domestic appliances, air-conditioners, automobiles) or computer peripherals whilst maintaining high metrological performance and reliability.

All these objects, as well as others which will be apparent in the following, are achieved through a capacitive sensor for measuring humidity which includes two electrodes separated by a dielectric material, characterized in that one of the electrodes is formed by means of non-porous metal foil. Advantageously, the other electrode is formed by a porous any but metal material positioned as a thick layer and made conductive by inclusion of a plurality of electrically conductive particles. In reference to the prior art, it was seen above that if they were made of metal, these electrodes had to meet two criteria which may be difficultly compatible with one another; on the one hand, they should exhibit the lowest possible pressure drop (porosity) in order to bring the material forming the dielectric (polymer) into equilibrium with the surrounding gas; on the other hand, they should provide electric continuity. These results are only obtained by vacuum-depositing a metal in a thickness which is relatively large for providing electric continuity and sufficiently thin in order to avoid that the electrode behaves as a continuous film preventing any gas exchange, which would preclude use of the condenser as a humidity sensor. According to the present invention, this contradiction is resolved in that one of the electrodes is formed by a non-porous metal foil and the other one by a non-metal porous material positioned as a thick layer and made conductive by inclusion of a plurality of electrically conductive particles. The term "porous" is used herein the sense of not been totally impervious to steam.

Use of an electrode in the form of a non-porous metal foil provides several advantages: first of all, the metal strip which is massive metal, directly serves as a substrate for depositing the dielectric, whereas in the prior art, the metal was vacuum-deposited on a glass substrate for example, which causes the coating to be heterogeneous, both with respect to its nature and its level. Actually, when the metal is deposited, it does not cover either uniformly or totally the substrate surface; therefore, in some places, there are voids in the metal and in some other places, wavelets due to an excess in thickness of the coating. All these drawbacks are eliminated with the invention by using a perfectly rolled strip with a mirror polished finish which therefore is a unique and continuous material free from any shift in level. In addition, this massive strip acts as a barrier in such a way that steam remains trapped in the dielectric and not in the electrode.

Preferably, the material forming the porous electrode is to be selected from polymers, with which a lack of imperviousness may be achieved, including with a relatively large thickness (preferably of the order of 25 to 100 microns). This material will be made conductive by doping, i.e. by inclusion of electrically conductive particles) such as metal particles, into the mass. For instance, a resistivity of about 10 to 50 Ω should be suitable. An identical result may be obtained by selecting any plastic material in such a thickness that it is not completely impervious, wherein said material is made electrically conductive by any suitable means.

Another characteristic advantage of the sensors according to the invention, is that they include a dielectric formed by a polymer film deposited as a plurality of layers of uneven thicknesses; this method allows for better control of the final thickness and of the evenness of the dielectric which has favorable consequences on the precision of the thereby produced condensers. This layout contributes to obtaining condensers having constant sensitivity (Delta C on C) and so they may be interchanged easily. It should be noted that such a dielectric polymer film may be used and applied with all types of electrodes, including those of the prior art produced by depositing a metal.

In spite of these precautions, it is seen that optimal accuracy on the value of the capacity for a given moisture content is not always achieved. Considering the manufacturing method, adjustment of the condenser may be carried out very easily and very rapidly: indeed, it is sufficient to reduce the useful surface of the porous electrode until the desired value is obtained; this operation may be performed by simple scraping or erosion of the material forming the porous electrode.

It should be realized that according to this method of manufacture it is possible to obtain sensors with particularly low commercial costs. In addition to their accuracy and reproducibility properties, these condensers will prove to be particularly robust and may, withstand large and various mechanical and/or thermal stresses without any damages. They should exhibit great flexibility, so that they may be used on any but plane surfaces. Finally, tapping of information will be performed in a very simple manner, preferably by means of direct contacts on both of the two electrodes. Flexible condensers may thus be provided which are intended to be placed on circuits or in existing assemblies simply by using clips. Incidentally, it should be noted that this method of tapping information was unfeasible with condensers built according to the prior art, because the thin thickness and the brittleness of the porous metal electrode prevented any installation of a wire connection on said electrode.

In addition to condensers to be used as humidity sensors, the present invention relates to the manufacturing method for these sensors. For the preferred embodiment, this method relates to the successive stacking of a metal foil as base substrate, of a porous dielectric polymer film and of a doped porous polymer layer. The elementary condensers are therefore obtained by cutting out the above described stacks. It is possible to adjust the value of the capacity by acting on the useful surface of at least one of the electrodes. Finally, tapping of information may be achieved by simple contacts on the external faces of the electrodes to such an extent that the condensers according to the invention do not need to be provided with connecting wires.

BRIEF DESCRIPTION OF THE DRAWINGS

Other advantages and features of the invention will become apparent after discussion of a preferred embodiment and variant of the invention hereafter, given as an illustration, and of appended drawings wherein.

DETAILED DESCRIPTION OF THE INVENTION

Figure 1:
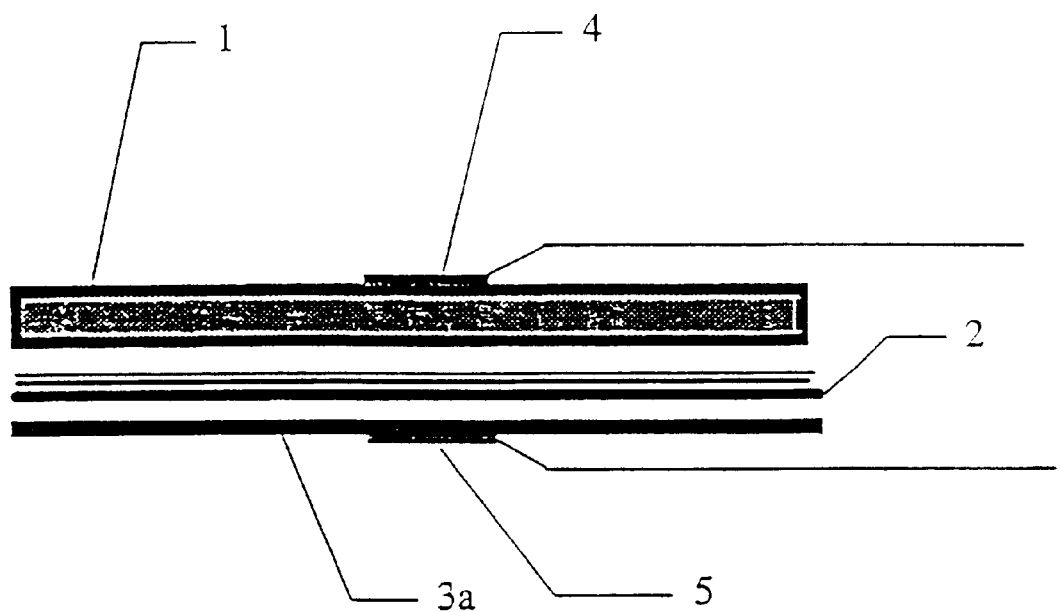
FIG. 1 represents a sectional view of a capacitive sensor according to the invention, according to the preferred embodiment.

In FIG. 1 it is seen that the condensers according to the invention are produced by stacking a metal foil used as a first electrode 3a, a polymer film 2 of low thickness (about 2 microns) wherein said film is preferably produced by stacking films of uneven thicknesses, or a second electrode 1 made in a doped any but metal material (for example a polymer), wherein said second electrode exhibits a thickness of about 100 microns and an effective resistance of the order of 10 to 50 Ω. The information tapping contacts 4 and 5 are directly made on electrodes 1 and 3a, respectively.

In the manufacturing process, the metal foil directly serves as base substrate for depositing the dielectric 2 and the porous electrode 1. Within the scope of industrial mass production, this foil will be selected with large dimensions and the thus achieved complex will be cut out to the exact dimensions of the condensers.

Figure 2:
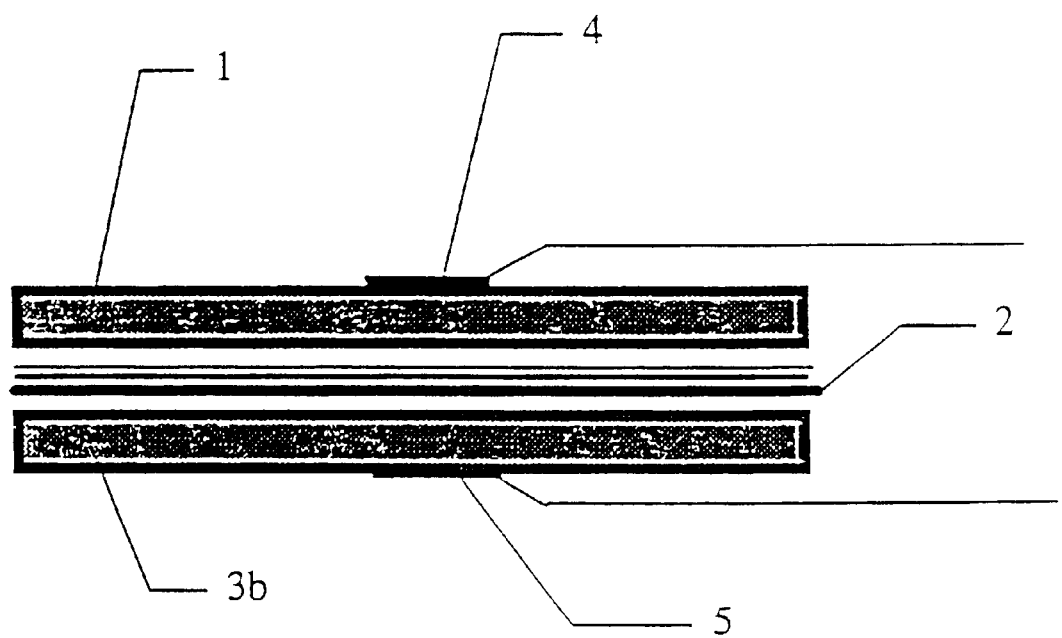
FIG. 2 represents a sectional view of a capacitive sensor according to a variant with two porous electrodes.

In a variant represented in FIG. 2, condensers provided with two porous electrodes for example, separated by a multilayer dielectric polymer film obtained by depositing layers of different thicknesses may optionally be made. The following stack would thus be formed:

- a polymer layer having been made into an electric condenser by doping.
- a multilayer polymer film
- a polymer layer having been made electrically conductive by doping.

Once more, tapping of information should be achieved by direct contacts on both porous electrodes, such condensers will form particularly effective humidity sensors; in particular, they will be in practically complete osmosis with the medium, resulting in further increased sensitivity and particularly short response times.

Of course, the above description is only given as an illustration and other embodiments of the condensers and especially those of different dimensions may be selected without departing from the scope of the present invention.

What is claimed is:

1. A capacitive humidity sensor including two electrodes separated by a dielectric material, one of the electrodes being produced by means of a metal foil, characterized in that the other electrode is in direct contact with the dielectric material and is formed by a porous non-metal material as a thick layer and made conductive by inclusion of a plurality of electrically conductive particles.

2. A humidity sensor according to claim 1, characterized in that the porous material forming the electrode is selected from polymers.

3. A humidity sensor according to claim 1, characterized in that the porous material forming the electrode is a plastic material exhibiting a thickness so as not to be totally impervious.

4. A humidity sensor according to claim 1, characterized in that the porous electrode exhibits a thickness on the order of 25 to 100 microns.

5. The capacitive humidity sensor according to claim 1, wherein said one of the electrodes is a non-porous metal foil.

6. A capacitive sensor for measuring humidity including two electrodes separated by a dielectric material, one of the electrodes being produced by means of a metal foil, characterized in that the other electrode is in direct contact with the dielectric material and is formed by a porous non-metal material positioned as a thick layer and made conductive by inclusion of a plurality of electrically conductive particles; and wherein the porous electrode exhibits an effective resistance on the order of 10 to 50 $\Omega$.

7. The capacitive sensor according to claim 6, wherein said one of the electrodes is a non-porous metal foil.

8. A capacitive sensor for measuring humidity including two electrodes separated by a dielectric material, one of the electrodes being produced by means of a metal foil, characterized in that the other electrode is in direct contact with the dielectric material and is formed by a porous non-metal material positioned as a thick layer and made conductive by inclusion of a plurality of electrically conductive particles; and wherein said dielectric material is provided in the form of a polymer film comprising a plurality of stacked layers of uneven thicknesses.

9. The capacitive sensor according to claim 8, wherein said one of the electrodes is a non-porous metal foil.

10. A capacitive sensor for measuring humidity including two electrodes separated by a dielectric material, one of the electrodes being produced by means of a metal foil, characterized in that the other electrode is in direct contact with the dielectric material and is formed by a porous non-metal material positioned as a thick layer and made conductive by inclusion of a plurality of electrically conductive particles; and characterized in that information tapping is achieved by a direct contact on each of the two electrodes.

11. The capacitive sensor according to claim 10, wherein said one of the electrodes is a non-porous metal foil.

12. A method for manufacturing a capacitive sensor for measuring humidity including two electrodes separated by a dielectric material, one of the electrodes being produced by means of a metal foil, characterized in that the other electrode is in direct contact with the dielectric material and is formed by a porous non-metal material positioned as a thick layer and made conductive by inclusion of a plurality of electrically conductive particles; said method characterized in that the method consists in producing a successive stacking of a metal foil, of an insulating multilayer polymer film, and of a doped polymer layer.

13. A method for manufacturing a capacitive sensor according to claim 12, wherein the desired value for a particular condenser is adjusted by reducing the useful surface of the porous electrode, wherein said reduction step is advantageously achieved by simple scraping or erosion of the material forming the porous electrode.

14. The capacitive sensor according to claim 12, wherein said one of the electrodes is a non-porous metal foil.

15. A capacitive humidity sensor for measuring humidity, comprising:

a first electrode;

a second electrode;

a dielectric material between said first electrode and said second electrode; and wherein said first electrode is a metal foil;

said second electrode is a porous non-metal material and made conductive by inclusion of a plurality of electrically conductive particles; and said dielectric material has a dielectric constant that varies substantially with a change in humidity so that said humidity sensor provides correspondingly varying capacitance with the change in humidity, thereby providing a measurement of the humidity.

16. The capacitive humidity sensor according to claim 15 wherein said second electrode is thicker than said first electrode.

17. The capacitive humidity sensor according to claim 15, wherein said second electrode is in direct contact with said dielectric material.

18. The capacitive humidity sensor according to claim 15, wherein said second electrode exhibits a thickness on the order of 25 to 100 microns.

19. The capacitive humidity sensor according to claim 15, wherein said second electrode exhibits an effective resistance on the order of 10 to 50 $\Omega$.

20. The capacitive humidity sensor according to claim 15, wherein said dielectric material is provided in the form of a polymer film comprising a plurality of stacked layers of uneven thicknesses.

21. The capacitive humidity sensor according to claim 15, wherein information tapping is achieved by a direct contact on each of said first electrode and a said second electrode.

22. The capacitive humidity sensor according to claim 15, wherein said first electrode is a non-porous metal foil.

23. A method for manufacturing a capacitive sensor, comprising the steps of:
  (1) providing a first electrode, a second electrode, and a dielectric material, wherein the first electrode is a metal foil; the second electrode is a porous non-metal material and made conductive by inclusion of a plurality of electrically conductive particles; and the dielectric material is a multilayer polymer film having a dielectric constant that that varies substantially with a change in humidity so that the humidity sensor provides correspondingly varying capacitance with the change in humidity; and
  (2) successively stacking the first electrode, the dielectric material, and the second electrode; and
  (3) adjusting a desired value for a particular condenser by reducing a useful surface of the second electrode, wherein said reduction is achieved by scraping or eroding material forming the second electrode.

\* \* \* \* \*